(12) United States Patent
Büchner et al.

(10) Patent No.: US 8,241,869 B2
(45) Date of Patent: Aug. 14, 2012

(54) FERMENTATION DEVICE COMPRISING A COUPLED SUBSTRATE AND SEDIMENT TRANSPORT MECHANISM AND METHOD FOR OPERATING THE FERMENTATION DEVICE

(75) Inventors: Thomas Büchner, Kreischa (DE); Gerhard Langhans, Dresden (DE); Urs Haller, Urtenen-Schönbühl (CH); Roland Sickinger, Nehren (DE)

(73) Assignee: STRABAG Umweltanlagen GmbH, Dresden (DE)

( * ) Notice: Subject to any disclaimer, the term of this patent is extended or adjusted under 35 U.S.C. 154(b) by 875 days.

(21) Appl. No.: 12/096,083

(22) PCT Filed: Nov. 30, 2006

(86) PCT No.: PCT/EP2006/011518
§ 371 (c)(1), (2), (4) Date: Jan. 23, 2009

(87) PCT Pub. No.: WO2007/065597
PCT Pub. Date: Jun. 14, 2007

(65) Prior Publication Data
US 2010/0062482 A1    Mar. 11, 2010

(30) Foreign Application Priority Data
Dec. 5, 2005 (DE) .......................... 10 2005 057 978

(51) Int. Cl.
C12P 1/00 (2006.01)
C12P 7/08 (2006.01)
C12M 1/107 (2006.01)
C12M 1/00 (2006.01)
C12M 3/00 (2006.01)

(52) U.S. Cl. .............. 435/41; 435/300.1; 435/289.1; 435/163

(58) Field of Classification Search ................ None
See application file for complete search history.

(56) References Cited

U.S. PATENT DOCUMENTS
5,521,092 A    5/1996    Rindelaub et al.
2005/0029189 A1*    2/2005    Langhans et al. ............. 210/629

FOREIGN PATENT DOCUMENTS
DE    3239304 A    *    5/1984
DE    3239304 A1    5/1984
JP    10192677 A    7/1998
JP    2002143612 A    5/2002

* cited by examiner

*Primary Examiner* — Chris R Tate
*Assistant Examiner* — Russell Fiebig
(74) *Attorney, Agent, or Firm* — Gudrun E. Huckett

(57) ABSTRACT

A fermentation device for biological degradation of substrate containing organic material and for recovery of biogas produced by degradation has an elongate closed container having a first end and a second end opposite the first end. The first end has an inlet opening for untreated substrate and the second end has at least one removal opening for treated substrate. The container has at least one removal opening for biogas. The container has several reaction cells provided with individually driven mixing units. The mixing units have mixing unit shafts positioned transversely to a longitudinal extension of the container and mixing impellers mounted on the mixing unit shafts and driven on a circular path. The mixing unit shafts are arranged at axial spacings smaller than a diameter of the mixing units so that the mixing impellers when the mixing unit shafts rotate pass trough an overlap range.

4 Claims, 1 Drawing Sheet

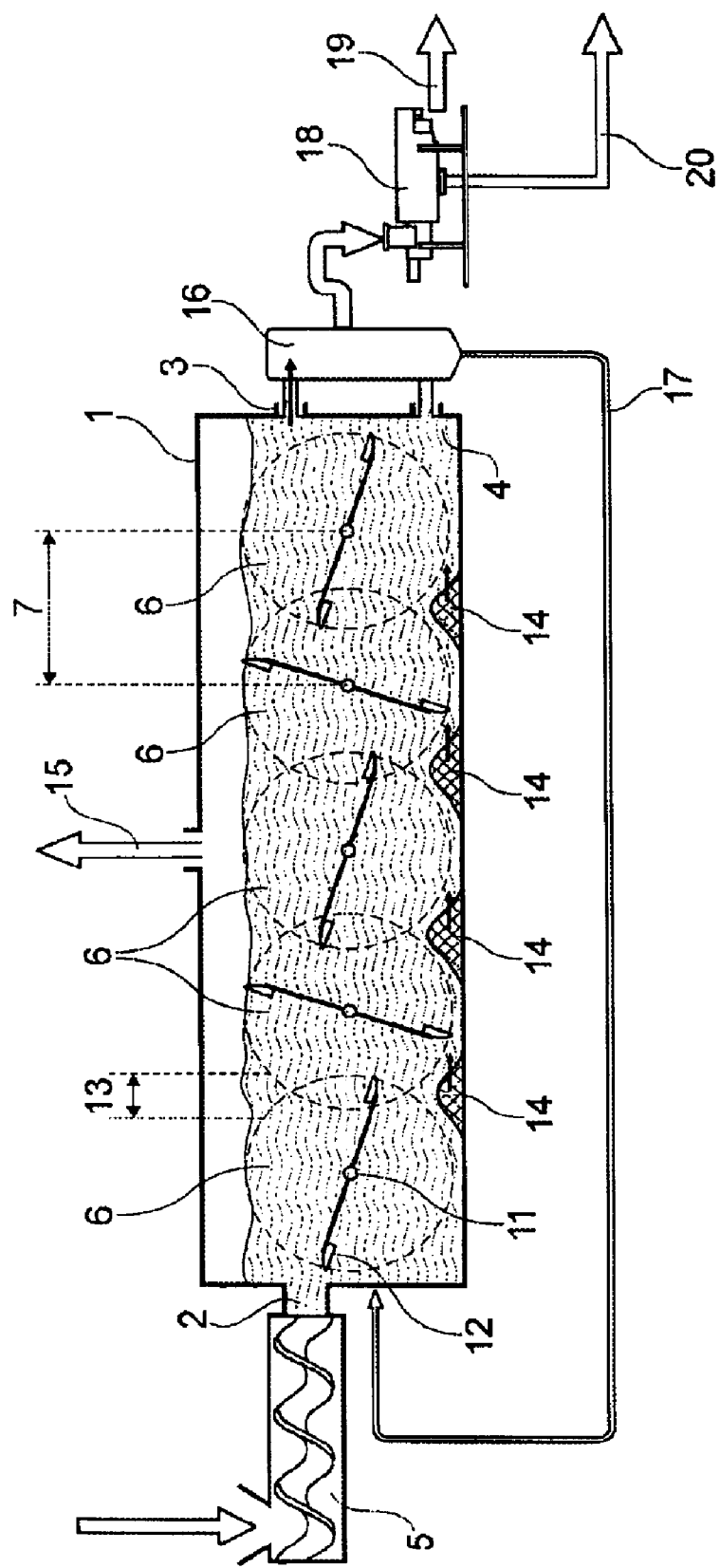

FERMENTATION DEVICE COMPRISING A COUPLED SUBSTRATE AND SEDIMENT TRANSPORT MECHANISM AND METHOD FOR OPERATING THE FERMENTATION DEVICE

BACKGROUND OF THE INVENTION

The invention concerns a fermentation device for biological degradation of a substrate containing organic material and for recovering biogas generated in the degradation process, comprising an elongate closed container with an inlet opening for the substrate at one end and an outlet opening for the treated substrate at the opposite end of the container as well as at least one removal opening for biogas, wherein the container has several reaction cells that contain, respectively, several individually driven mixing units for circulating the substrate, with mixing impellers moved on a circular path and with mixing unit shafts that are positioned transversely to the longitudinal extension of the container, as well as a method for operating the fermentation device.

When fermenting a substrate containing organic material, for example, biowaste, residues of food production, or renewable raw materials, a differentiation is made between the so-called wet fermentation and the so-called dry fermentation. While in wet fermentation a flowable suspension of the substrate is produced that is treated in a biogas reactor, for example, a loop reactor with internal loop flow, the substrate in dry fermentation is introduced, for example, at one end into a closed horizontal container, is circulated by means of a mixing device with generation of biogas, and the treated substrate is removed at the other end of the container.

The methods of dry fermentation are used alternatively to those of wet fermentation when the substrate to be treated anaerobically has a very high solids contents and therefore the required dilution to the operating range of the wet method with a solids concentration of less than approximately 15% is uneconomical or when the frequently required cost-intensive removal of unwanted material in wet methods is not required for other process-technological reasons. Dry fermentation is carried out preferably for solids contents of equal to or less than 35% at the fermenter inlet and can be performed in upright or horizontal reactors.

Advantages of dry fermentation when used in waste and residual waste treatment are the comparatively minimal pretreatment and conditioning expenditures for the received feedstock before fermentation. After removal of coarse unwanted material and subsequent commination of the batch for fermentation to 20 to 60 mm, generally there is no need for further removal of unwanted material, for example, wood, plastics, glass as well as sand and stones.

This minimal technological expenditure for initial treatment is counterbalanced by possible problems in the fermenter itself. As a result of the biochemical conversion of organic compounds in the fermentation medium across the fermenter length, the solids concentrations are reduced between the inlet opening and the removal opening from approximately 35% dry material to less than 20% dry material and the viscosity is reduced from 30,000 to 60,000 mPas down to less than 5,000 mPas. While in the solids-rich feedstock the afore mentioned unwanted materials capable of sedimentation and floating have been distributed substantially stationarily, they are now mobilized by the changing material properties of the fermentation medium in the fermenter which tends to result in the formation of sinking and floating layers. The mixing devices that are usually provided in the fermenter for improving the material transfer and degassing of the medium further enhance this fractioned separation.

Therefore, especially in horizontal dry fermenters there are also special devices provided for the transport and removal of sediments in addition to the mixing devices.

For example, in EP 0 617 120 B1 special scrapers are disclosed that transport the sediments at the bottom of the fermenter by means of movements transmitted by push rods to the end of the reactor in the direction of the thinning medium.

In this known construction, it is thus necessary to provide separate devices for mixing and for removal of unwanted materials; this increases the technological expenditure and the operational expenditure. In particular, servicing and elimination of malfunctions cause significant problems because they may require removal of the fermenter from the site.

SUMMARY OF THE INVENTION

The present invention has the object to design a fermentation device of the aforementioned kind as well as a method for operating the fermentation device in such a way that, in addition to the actual homogenization and degassing functions of the mixing devices, without impairment of the plug flow characteristics for the solid material stream between the inlet an outlet of the fermentation device, a sediment movement to the end of the fermentation device is induced and the generation of solidified floating layers is prevented at the same time.

This object is solved according to the invention in the fermentation device in that the mixing unit shafts are arranged at axial spacings that are smaller than the diameter of the mixing unit so that the mixing impellers upon rotation of the mixing unit shafts pass across an overlapping area.

The invention is based on the prior art device as disclosed in EP 0 617 120 B1. This known fermentation device has separately controllable transversely positioned mixing units that divide the fermenter into a series of sequentially connected fictitious reaction cells (mixing cells). The paddle wheel-like paddle mixers effect in their respective mixing cell a vertical media exchange inclusive of a floating layer dispersion of the floating cover by means of the mixing paddles that emerge from the liquid while the horizontal plug flow is produced by the combination of fermentation material removal and metered substrate addition. The sediment transport is realized separately by means of a pusher frame. The mixing unit shafts in the known fermentation device are arranged in the fermenter in such a way that the spacing of the mixing unit shafts relative to one another is greater than the mixing unit diameter.

Based on theoretical concepts that have been experimentally proven, it has been found surprisingly that this mixing system can be used also for a targeted sediment transport along the fermenter bottom. For this purpose, the effect of horizontal shifting by material transport from luff to lee which effect is known in connection with shifting sand dunes is utilized. Transport vehicles in this connection are the mixing impellers that for an appropriately designed spacing to the reactor bottom push the sediments to form a dune extending transversely to the longitudinal axis of container. For the currently employed conventional mixing unit geometries and axial spacings, this transportation process is however ineffective and can come to a complete stop or can lead to stalling of the mixing units, depending on the dry substance contents, media viscosity, and proportion of unwanted material.

In a preferred embodiment of the invention, the mixing impellers have at their outer ends paddles that are divided across the width of container and are arranged in a staggered alternating arrangement. It has been found that the sediment dunes should be kept small enough to remain mobile. For this purpose, the paddles are divided across the reactor width and arranged alternatingly, preferably staggered at angles of 120 degrees and 90 degrees, on the mixing unit shaft. In combination with the special geometry of the mixing system according to which the mixing unit shafts are arranged at axial spacings that are smaller than the mixing unit diameter, the maximum height of the sediment collection in the dead spaces between the rotating paddles can be geometrically predetermined in the desired way. For rotation in the same direction of the neighboring mixing units, the sediment is collected at one side and is then removed on the opposite side by means of the meshing staggered-operating paddles of the downstream mixing unit and transported across the bottom to the next dune. By means of the paddles that are divided in the transverse direction and positioned in a staggered arrangement on the shaft, it is prevented that the paddles will simultaneously immerse in the sediment across the entire width which could cause damage as a result of mechanical overload. Moreover, no coarse materials can laterally jam between the paddles and the container.

Expediently, in the removal area of the fermentation device a suction socket is provided near the bottom for removal of the sediments that have been moved there. In particular for the treatment of fermentation media with special sediment properties, according to a further embodiment of the concept of the present invention, in the removal area of the fermentation device a collecting pocket with slanted walls is formed and the suction socket ends at its deepest point.

The invention further concerns a method for biological degradation of a substrate that contain organic material and for recovering biogas produced during degradation wherein the substrate is introduced into an elongate closed container, flows in the container through several reaction zones in which it is circulated by means of individually driven mixing units with mixing impellers that are moved on a circular path about axes positioned transversely to the longitudinal extension of the container, and wherein degradation products are removed from the container.

With regard to the method, the object is solved in that the mixing impellers of neighboring mixing units that are arranged at axial spacings smaller than the mixing unit diameter are controlled such that the mixing impellers operate in a meshing impeller-on-gap arrangement. In this way it is ensured that the mixing impellers of neighboring mixing units will not block one another.

Preferably, the mixing impellers of neighboring mixing units are moved in the same direction. With same rotational direction the sediment is collected on one side and is removed on the opposite side by the meshing staggered-operating paddle of the neighboring mixing unit and transported across the bottom to the next dune.

The invention is suitable for all fermentation devices that have a horizontal container with transversely positioned mixing units. In particular when treating a substrate that has a great sedimentation tendency, the invention can be used at great advantage.

As a whole, the invention provides with minimal investment expenditure a technically elegant solution for simultaneous mixing of fermentation material and removal of the deposited sediments in the fermenter. A special advantage resides in that the plug flow characteristics relative to the substrate to be treated in the fermentation device is not disturbed by the sediment removal.

BRIEF DESCRIPTION OF THE DRAWING

In the following the invention will be explained in more detail with the aid of the embodiment schematically illustrated in the FIGURE.

The only Figure shows schematically a fermentation device according to the present invention comprising a horizontal container with inlet opening, removal openings and mixing units arranged transversely to the container axis.

DESCRIPTION OF PREFERRED EMBODIMENTS

The FIGURE shows a fermentation device with a horizontal closed container 1 that has at the end face end an inlet opening 2 for the substrate to be treated and at the other end removal openings 3 and 4. The substrate that is comprised, for example, of biowaste or renewable raw materials is introduced by means of a screw feeder 5 into the inlet opening 2 of the container 1. In the container 1, mixing units 6 are arranged transversely to the container axis; they each have a mixing unit shaft 11 that is oriented transversely to the container axis and is individually driven. On the mixing impellers of the mixing units 6 paddles 12 are mounted that are divided across the container width and are arranged alternatingly at angles of 120 degrees relative to one another on the mixing shaft. Moreover, the mixing shafts 11 are arranged at axial spacings that are smaller than the mixing unit diameter so that meshing of the paddles 12 is effected. The overlap area (meshing zone) of neighboring mixing units 6 is identified by reference numeral 13. By geometric determination of the axial spacings 6 as well as of the mixing unit diameter in the construction phase, the maximum height of the sediment deposit 14 in the dead spaces between the rotating paddles 12 can be predetermined technologically in the desired way. For identical rotational direction of the neighboring mixing units 6 the sediment is collected on one side and is removed on the opposite side by means of the meshing staggered-operating paddles of the following mixing unit and transported across the bottom of the next dune. The biogas that is produced during treatment in the container is removed through removal opening 15 from the container 1. The sediment dunes 14 that are transported to the end of the fermenter reach the area of the removal opening 4 where dry substance and sediment-enriched bottom fractions are removed by suction from the container 1. Liquid low in solids is removed in the upper area of the container through removal opening 3. In a downstream container 16 the fermentation material is separated and supplied to a dewatering press 18. The separated fermentation residues are then removed by a removal line 19 while the squeezed water is removed through line 20, for example, as liquid fertilizer. By means of a return line 17, fermentation material and the squeezed water are, if needed, returned to the end face end of the container 1.

What is claimed is:

1. A dry fermentation device for biological degradation of substrate containing organic material capable of sedimentation and for recovery of biogas produced by degradation, the device comprising:

an elongate closed container having a longitudinal axis, the container having a first end and a second end opposite the first end in axial direction of the longitudinal axis;

wherein the first end has an inlet opening for untreated substrate and the second end has at least one removal opening for treated substrate;

the container further having at least one gas removal opening for biogas;

the container having several reaction cells, wherein each reaction cell is provided with one individually driven mixing unit;

the driven mixing units comprising mixing unit shafts, positioned transversely to the longitudinal axis of the container and axially spaced relative to each other in the axial direction, and mixing impellers mounted on the mixing unit shafts and driven on a circular path for mixing the substrate;

the mixing impellers having outer ends provided with paddles;

the mixing impellers of neighboring mixing units being rotated in the same direction;

the mixing unit shafts arranged at axial shaft spacings smaller than a diameter of the mixing units so that the mixing impellers, when the mixing unit shafts rotate, pass through an overlap range such that, in operation, the mixing units transport sediments along the bottom of the container from the first end to the second end by pushing sediments to form a dune that extends transversely to the longitudinal axis of the container, by collecting the sediments on one side of the dune, by removing the sediments on the opposite side of the dune, and by transporting the removed sediment across the bottom of the container to the next dune.

2. The dry fermentation device according to claim 1, wherein the paddles are divided across a width of the container and are arranged in an alternating staggered arrangement.

3. The dry fermentation device according to claim 1, wherein the at least one removal opening is a suction socket for removing sediments, wherein the suction socket is arranged near a bottom of the container.

4. The dry fermentation device according to claim 3, wherein the container has a collecting pocket comprised of slanted walls and wherein the suction socket is connected to a deepest point of the collecting pocket.

* * * * *